United States Patent [19]

Martin et al.

[11] Patent Number: 6,127,424
[45] Date of Patent: Oct. 3, 2000

[54] ARYL-SUBSTITUTED CYCLOBUTYLALKYLAMINES FOR TREATING OBESITY

[75] Inventors: Keith Frank Martin; David John Heal, both of Nottingham, United Kingdom

[73] Assignee: Knoll Aktiengesesllschaft, Ludwigshafen, Germany

[21] Appl. No.: 08/952,285

[22] PCT Filed: May 24, 1996

[86] PCT No.: PCT/EP96/02239

§ 371 Date: Apr. 27, 1998

§ 102(e) Date: Apr. 27, 1998

[87] PCT Pub. No.: WO96/38134

PCT Pub. Date: Dec. 5, 1996

[30] Foreign Application Priority Data

May 29, 1995 [DE] Germany .......................... 195 18 988

[51] Int. Cl.[7] ................................................. A61K 31/137
[52] U.S. Cl. ........................ 514/646; 514/656; 514/657
[58] Field of Search .................................. 514/646, 656, 514/657

[56] References Cited

FOREIGN PATENT DOCUMENTS

| | | |
|---|---|---|
| 1575593 | 9/1980 | United Kingdom . |
| 2098602 | 11/1982 | United Kingdom . |
| 88/06444 | 9/1988 | WIPO . |
| 90/06110 | 6/1990 | WIPO . |
| 94/00047 | 1/1994 | WIPO . |
| 94/00114 | 1/1994 | WIPO . |
| 94/26704 | 11/1994 | WIPO . |

OTHER PUBLICATIONS

Witiak et al., *J. Med. Chem.*, vol. 15, No. 8, pp. 803–808 (1972).
Luscombe et al., Int. Symp. on Antidep., Jerusalem, Apr. 1987 (37).
Martin et al., *Soc. Neur. Abst.*, 19/1–3 (297) 1993.
Scott et al., *Br. J. Pharmacol.*, 104/Proc. Supp. Oct. (244), 1991.
M.T. Mahony, *Diss. Abst. Int. B*, 52/11 (5773) 1992.
Kaiser et al., *J. Clin. Pharm.*, 34/10 (1019) 1994.
Scott et al., *Br. J. Pharm.*, 111/Proc. Suppl. (167) 1994.
Scott et al., *Br. J. Pharm.*, 111/1 (97–102) 1994.
Cheetam et al., *Neuropharmacology*, 32/8 (737–43) 1993.
Pinder et al., *Med. Res. Rev.*, 13/3 (259–325) 1993.
Heal et al., *Psychopharmacology*, 107/2–3 (303–09) 1992.
Cheetham et al. *Br. J. Pharm.*, 101/Suppl. (515) 1990.
Luscombe et al., *Psychopharmacology*, 100/3 (345–49) 1990.
M.T. Mahony et al., *Br. J. Pharm.*, 98/Dec. Proc. Suppl. (877) 1989.
Luscombe et al., *Neuropharmacology*, 28/2 (129–34) 1989.
M.T. Mahony et al., *Br. J. Pharm.*, 95/Dec. Suppl. (885) 1988.
Luscombe et al., *Br. J. Pharm.*, 92/Dec. Suppl. (575) 1987.

*Primary Examiner*—Phyllis G. Spivack
*Attorney, Agent, or Firm*—Keil & Weinkauf

[57] ABSTRACT

Use of aryl-substituted cyclobutylalkylamines and their pharmaceutically suitable salts for treating obesity and its accompanying disorders are disclosed.

24 Claims, 3 Drawing Sheets

FIG.A
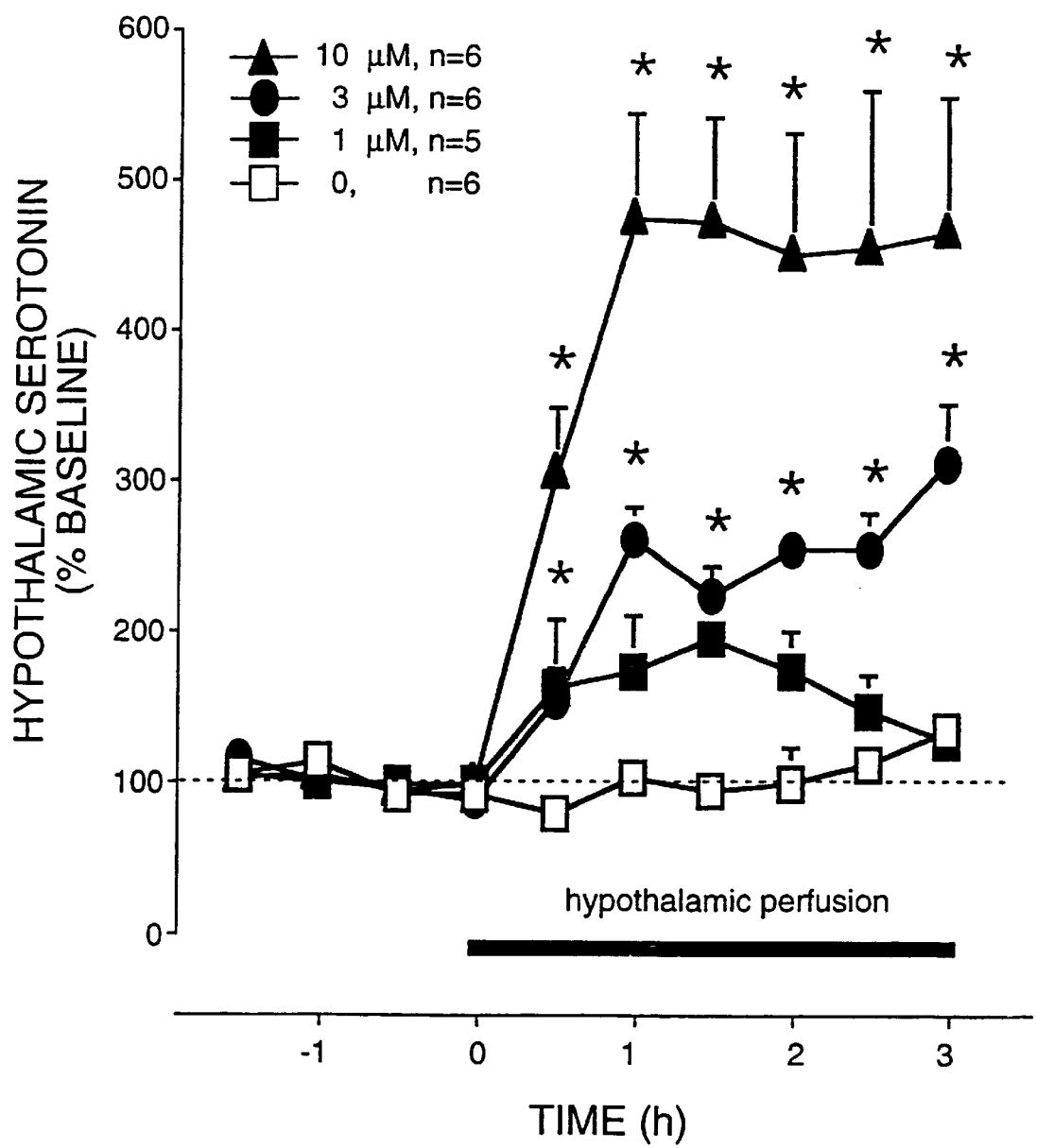

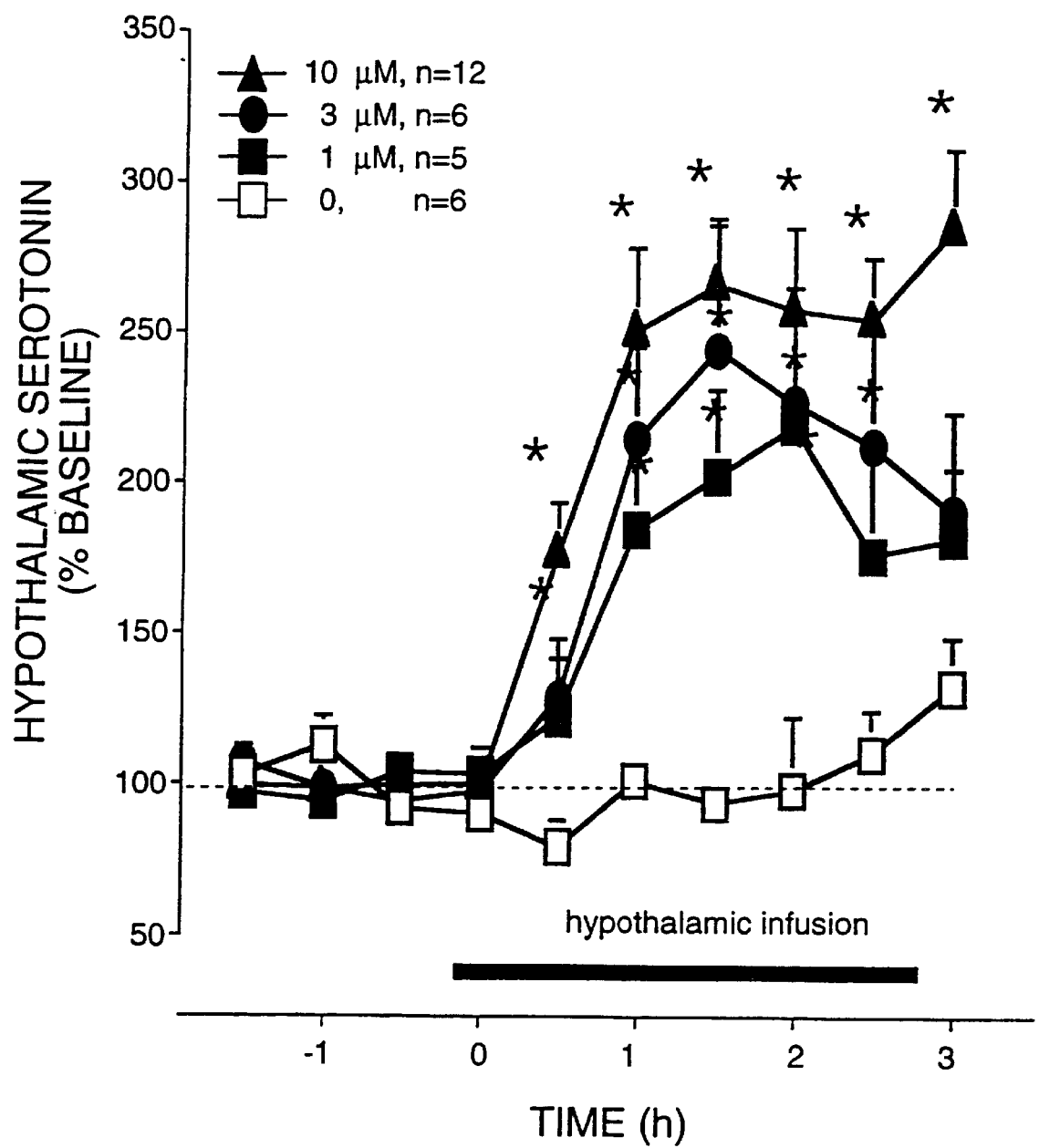
FIG.B

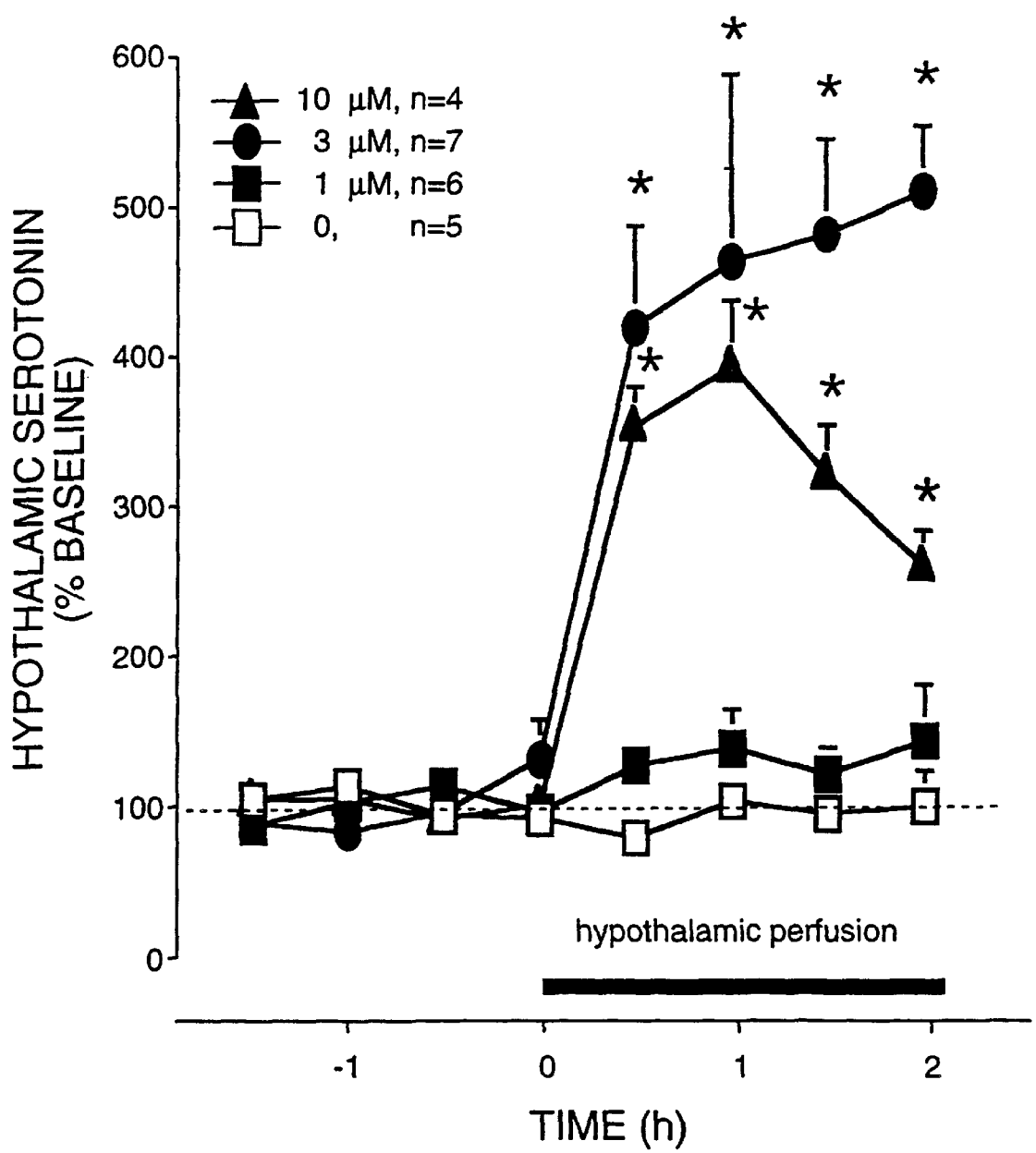
FIG.C

ARYL-SUBSTITUTED CYCLOBUTYLALKYLAMINES FOR TREATING OBESITY

The invention relates to use of aryl-substituited cyclobutylalkylamines for treating obesity. DE 32 12 682 C2 discloses aryl-substituted cyclobutylalkylamines. The compounds disclosed therein are employed as antidepressants.

WO 90/06110 discloses the use of N,N-dimethyl-1-1[1-(4-chlorophenyl)cyclobutyl]-3-methylbutylamine hydrochloride for treating obesity.

It has now been found, surprisingly, that a certain group of the compounds disclosed in DE 32 12 682 C2 is more suitable for treating obesity than the hydrochloride described in WO 90/06110 for this purpose. The present invention therefore relates to the use of aryl-substituted cyclobutylalkylamines of the formula I

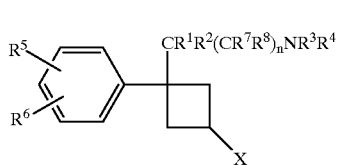

where n is 0 or 1, $R^1$ is, when n is 0, a straight-chain or branched-chain alkyl group having 1 to 6 carbon atoms, a cycloalkyl group having 3 to 7 carbon atoms, a cycloalkylalkyl group in which the cycloalkyl group contains 3 to 6 carbon atoms and the alkyl group contains 1 to 3 carbon atoms, an alkenyl or an alkynyl group having 2 to 6 carbon atoms, it being possible for the alkyl group, the cycloalkyl group, the cycloalkylalkyl group, the alkenyl or alkynyl group to contain at least one substituent which is selected from the group consisting of hydroxyl and acylated derivatives thereof, alkoxy groups, unsubstituted or substituted by hydroxyl, oxo, alkoxy, carbamoyl, carbocyclic or heterocyclic groups, cycloalkyloxy groups having 3 to 6 carbon atoms, alkylenedioxy groups, oxo- and groups of the formula $S(O)_p R^5$, where p is 0, 1 or 2, and $R^5$ is an alkyl group having 1 to 3 carbon atoms, it being possible for the aliphatic group to be substituted by other substituents selected from carbocyclic groups having 3 to 6 carbon atoms, heterocyclic groups or halogen atoms, or a group of the formula II

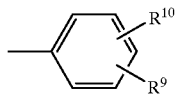

where $R^9$ and $R^{10}$, which can be identical or different, are a hydrogen atom, a halogen atom or an alkoxy group having 1 to 3 carbon atoms, and, when n is 1, a hydrogen atom or an alkyl group having 1 to 3 carbon atoms, $R^2$ is a hydrogen atom or an alkyl group having 1 to 3 carbon atoms, $R^3$ is a hydrogen atom, $R^4$ is a hydrogen atom, a straight-chain or branched-chain alkyl group having 1 to 4 carbon atoms, an alkenyl group having 3 to 6 carbon atoms, an alkynyl group having 3 to 6 carbon atoms, or a cycloalkyl group in which the ring contains 3 to 7 carbon atoms, or $R^4$ is CHO, $R^5$ and $R^6$, which can be identical or different, are a hydrogen atom, a halogen atom, a trifluoromethyl group, an alkyl group having 1 to 3 carbon atoms, an alkoxy or alkylthio group having 1 to 3 carbon atoms or a phenyl group, or together with the carbon atoms to which they are bonded form a second benzene ring which is unsubstituted or substituted by one or more halogen atoms, one alkyl or alkoxy group having 1 to 4 carbon atoms, or the substituents in the second benzene ring form, together with the two carbon atoms to which they are bonded, another benzene ring, and $R^7$ and $R^8$, which can be identical or different, are a hydrogen atom or an alkyl group having 1 to 3 carbon atoms, and X is a hydrogen atom or a hydroxyl group, and their pharmaceutically suitable salts, for treating obesity and its accompanying disorders.

The compounds used according to the invention have the advantage of very good bioavailability and show a more favorable spectrum of side effects.

In the formulae present in this description and the claims, the symbol

means a 1,1-disubstituted cyclobutane group of the formula

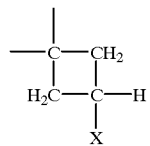

and $—CR^1R^2(CR^7R^8)_n NR^3R^4$ means a group of the following formula

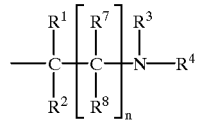

Preferred compounds of the formula I, in which n is 0 are those where $R^1$ is a straight-chain or branched-chain alkyl group having 1 to 4 carbon atoms, a cycloalkyl group having 3 to 7 carbon atoms, a cycloalkylmethyl group, in which the cycloalkyl ring contains 3 to 6 carbon atoms, or a group of the formula II in which $R^9$ and/or $R^{10}$ are a hydrogen atom, a fluorine atom or methoxy, and $R^2$ is a hydrogen atom or methyl. Examples of particularly preferred compounds of the formula I are those where $R^1$ is methyl, ethyl, propyl, isopropyl, butyl, sec-butyl, isobutyl, cyclopropyl, cyclobutyl, cyclopentyl, cyclohexyl, cyclopropylmethyl, cyclobutylmethyl, cyclopentylmethyl, cyclohexylmethyl and phenyl, if n is 0, and $R^2$ is a hydrogen atom.

Compounds of the formula I wherein n is 0 can alternatively be represented by formula Ia:

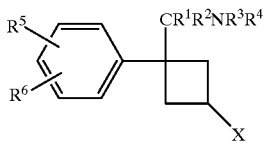

Ia

Preferred compounds of he formula I in which n is 1 are those where $R^1$ is a hydrogen atom or methyl, and $R^2$ is a hydrogen atom. Particularly preferred compounds of the formula I in which n is 1 are those where both $R^1$ and $R^2$ are each a hydrogen atom.

Preferred compounds of the formula I are those where $R^4$ is a hydrogen atom, methyl, ethyl or formyl.

Preferred compounds of the formula I are those where $R^5$ and/or $R^6$ is a hydrogen, fluorine, chlorine, bromine or iodine atom, trifluoromethyl, methyl, methoxy or phenyl, or $R^5$ and $R^6$ form, together with the carbon atoms to which they are bonded, a second benzene ring which is unsubstituted or substituted by halogen.

A first group of preferred compounds is represented by the formula III

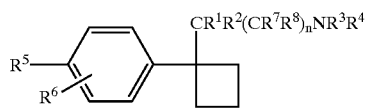

III

Compounds of the formula III wherein n is 0 can alternatively be represented by formula IIIa:

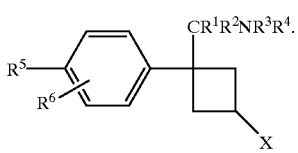

IIIa where $R^1$ to $R^8$ have the same meanings as above. Preferred compounds of the formula III are those where $R^5$ and $R^6$, which can be identical or different, are a hydrogen, fluorine, chlorine, bromine or iodine atom, trifluoromethyl, methyl, methoxy or phenyl, or $R^5$ and $R^6$ form, together with the carbon atoms to which they are bonded, a second benzene ring which is unsubstituted or substituted by a chlorine atom. Particularly preferred compounds of the formula III are those where $R^5$ and/or $R^6$ is a hydrogen, fluorine, chlorine or iodine atom, trifluoromethyl, methyl or phenyl, or $R^5$ and $R^6$ form, together with the carbon atoms to which they are bonded, a second benzene ring which is unsubstituted or substituted by a chlorine atom.

A second group of preferred compounds is represented by the following formula IV

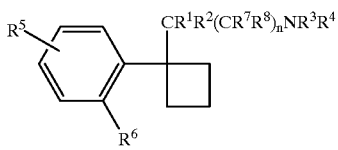

IV where $R^5$ can be a hydrogen, fluorine, chlorine, bromine or iodine atom, trifluoromethyl, methyl, methoxy or phenyl, and where $R^6$ is a fluorine atom or methyl. Particularly preferred compounds of the formula IV are those where $R^5$ is a hydrogen or chlorine atom.

Preferred compounds of the formula I in which n is 1 are those where $R^7$ is a hydrogen atom, methyl or ethyl, and $R^8$ is a hydrogen atom, and particularly preferred compounds of the formula I are those where $R^7$ is a hydrogen atom or ethyl and $R^8$ is a hydrogen atom.

Particularly preferred compounds of the formula III are those where $R^1$ is a $C_4$-alkyl radical, in particular isobutyl, $R^2$ is a hydrogen, n=0, $R^4$ is a $C_1$- or $C_2$-alkyl radical, $R^5$ is a chlorine atom and $R^6$ is a hydrogen.

Preferred compounds of the formulae I, III and IV are those where X is a hydrogen atom.

Compounds of the formula I can be in the form of salts with pharmaceutically suitable acids. Salts of inorganic and organic acids are suitable.

Examples of salts of these types comprise sulfates, hydrochlorides, hydrobromides, nitrates, phosphates, maleates, acetates, citrates, lactates, benzoates, arylsulfonates, alkylsulfonates, especially methane-, ethane-, propane and butanesulfonates, fumarates, gluconates, tartrates, succinates, tosylates and salts with acidic amino acids, such as aspartic acid or glutamic acid. Hydrochlorides, acetates, phosphates and tosylates are preferred.

Compounds of the formula I which contain one or more asymmetric carbon atoms can exist in various optically active forms. When $R^1$ and $R^2$ are different or $R^7$ and $R^8$ are different, the compounds of the formula contain a chiral center. Compounds of this type exist in two enantiomeric forms, and the present invention includes both the enantiomeric forms and the mixtures thereof. The dextrorotatory compounds have proven to be particularly preferred because they show distinctly greater activity than the levorotatory ones in reuptake inhibition experiments.

When both the radicals $R^1$ and $R^2$ and the radicals $R^7$ and $R^8$ are different, the compounds of the formula I contain two chiral centers, and the compounds exist in four diastereoisomeric forms. The present invention includes each of these diastereomeric forms and mixtures thereof.

The compounds of the formula I are used in pharmaceutical preparations which contain a therapeutically effective amount of a compound of the formula I together with a pharmaceutically suitable diluent or vehicle. For therapeutic use, the active compound can be administered orally, rectally, parenterally or topically, preferably orally. Accordingly, the therapeutic preparations of the present invention may have the form of any of the known pharmaceutical preparations for oral, rectal, parenteral or topical administration. Pharmaceutically suitable vehicles suitable for use in preparations of these types are known to the person skilled in the pharmaceutical art. The preparations of the invention may contain from 0.1 to 90% by weight of the active compound. The preparations according to the invention are usually produced in single-dose form.

Preparations for oral administration are the preferred preparations of the invention, and these are the known pharmaceutical forms for an administration of this type, for example tablets, capsules, syrups and aqueous or oily suspensions with acute or delayed release profile. The vehicles used to produce these preparations are those known to the person skilled in the pharmaceutical art. Tablets can be produced by mixing the active compound with an inert diluent such as calcium phosphate in the presence of dispersing or dissolving agents, for example corn starch and lubricants, for example magnesium stearates, and tabletting the mixture by known processes. The tablets can be formulated in a manner known to the skilled worker in order to ensure uniform release of the compounds of the present invention. Tablets of this type can, if required, be provided by known processes with coatings which dissolve only in the intestine, for example by use of cellulose acetate phthalate. It is possible in a similar way for capsules, for example hard or soft gelatin capsules which contain the active compound with or without added vehicle, to be produced by conventional processes and, if required, be provided in a known manner with coatings which dissolve only in the intestine. The tablets and capsules may each suitably contain from 1 to 500 mg of active compound. The tablets can also be produced by extrusion processes, with or without subsequent shaping. Extrusion processes of this type are known in the art (eg. EP 240 904, EP 240 906 and EP 358 105).

Other preparations for oral administration comprise, for example, aqueous suspensions which contain the active compound in an aqueous medium in the presence of a non-toxic suspending agent such as sodium carboxymethylcellulose, and oily suspensions which contain a compound of the present invention in a suitable vegetable oil, for example in arachis oil.

Preparations of the present invention suitable for rectal administration are the known pharmaceutical forms for an administration of this type, for example suppositories with cocoa butter or polyethylene glycol bases.

Preparations with compounds of the formula I suitable for parenteral administration are the known pharmaceutical forms for an administration of this type, for example sterile suspensions in aqueous or oily media, or sterile solutions in a suitable solvent.

Preparations for topical administration may contain a base in which the pharmacologically active compounds of the present invention are dispersed so that the compounds are kept in contact with the skin in order to administer the compounds transdermally. The active compounds can be dispersed as selected in a pharmaceutically suitable cream or ointment base.

It may be advantageous for some formulations to use the compounds of the present invention in the form of very small particles, for example those obtained by milling in an air jet mill.

The active compound can, if required, be combined with other suitable pharmacologically active ingredients in the preparations of the present invention.

The pharmaceutical preparations which contain a therapeutically effective amount of a compound of the formula I can be employed for treating human obesity. The amount of the compound of the formula I administered per day for such a treatment depends on various factors, eg. the age, and is normally in the range from 0.1 to 500 mg, preferably in the range from 1 to 100 mg, administered in one or more doses.

The compounds of the formula I can be prepared in a variety of ways.

The mode of preparation is known to the skilled worker and is described in detail, for example, in DE 32 12 682, which is incorporated herein by reference.

Compounds of the formula I where $R^4$ is CHO can be prepared, for example, by reductive amidation of ketones or aldehydes, for example with formamide and formic acid, or ammonium formate and formic acid to form compounds of the formula I where $R^4$ is CHO and $R^3$ is a hydrogen atom.

Compounds of the formula I where $R^4$ is CHO can also be prepared by formylation of compounds of the formula I where $R^4$ is a hydrogen atom, for example by reacting with methyl formate. Examples of suitable processes for reductive amination of ketones or aldehydes are indicated in DE 32 12 682.

Compounds of the formula I where $R^4$ is a hydrogen atom or an alkyl or cycloalkyl group are prepared by catalytic hydrogenation of a mixture of the ketone or aldehyde and an amine of the formula $HNR^3R^4$ at elevated temperature and pressure.

Compounds of the formula I can also be prepared by reducing corresponding precursors as described in detail in DE 32 12 682.

Compounds of the formula I where $R^4$ is a hydrogen atom can be prepared by decarboxylating rearrangement, for example using iodosobenzene bistrifluoroacetate, or by a Hofmann reaction using bromine in alkaline solution, of amides of the formula V or amides of the formula VI

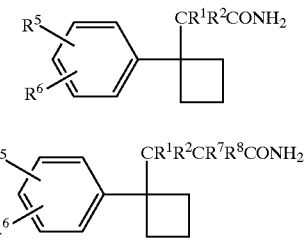

to form amines of the formula I where n is 0 or 1 respectively. Compounds of the formula I where $R^4$ is a hydrogen atom can also be prepared by decarboxylating rearrangement of acyl azides in a Curtius reaction. The acyl azides can be formed, for example, by reacting corresponding acid chlorides with sodium azide.

Compounds of the formula I where $R^4$ is a hydrogen atom can also be prepared by a Schmidt reaction, in which a corresponding carboxylic acid is reacted with hydrozoic acid. Compounds of the formula I where $R^4$ is a hydrogen atom can also be prepared by hydrolyzing compounds of the formula I where $R^4$ is CHO, for example by acid hydrolysis.

Compounds of the formula I where $R^4$ is methyl can be prepared by reducing compounds of the formula I where $R^4$ is CHO, for example with lithium aluminum hydride or with sodium bis(2-methoxyethoxy)aluminum hydride. Compounds of the formula I where $R^4$ is not a hydrogen atom can be prepared from compounds of the formula I where $R^4$ is hydrogen by processes known to the skilled worker for converting primary into secondary amines. Examples of suitable processes are indicated in detail in DE 32 12 682, which is incorporated herein by reference.

Compounds of the formula I where X is a hydroxyl group can be obtained by a tandem Grignard reaction of a 3-hydroxycyclobutane-1-phenyl-1-carbonitrile with isobutylmagnesium bromide, it also being possible to employ compounds with a protective group on the oxygen atom.

The preparation of the required intermediates such as the abovementioned ketones, aldehydes or amides, and their starting materials, is also described in detail in DE 32 12 682.

The individual enantiomers can be prepared by enantioselective synthesis from optically active precursors, or by fractionating the racemate which can be prepared as described above. Enantiomers of secondary amines of the formula I can also be prepared by preparing the racemate of the corresponding primary amine, fractionating the latter into the individual enantiomers, and then converting the optically pure primary amine enantiomer into the required secondary amine.

Specific enantiomers which may be mentioned as examples are:

(R)-(+)-N-{1-[1-(4-chlorophenyl)cyclobutyl]-3-methylbutyl}-N-methylamine;
(S)-(−)-N-{1-[1-(4-chlorophenyl)cyclobutyl]-3-methylbutyl}-N-methylamine;
(R)-(+)-1-[1-(4-chlorophenyl)cyclobutyl]-3-methylbutylamine;
(S)-(−)-1-[1-(4-chlorophenyl)cyclobutyl]-3-methylbutylamine.

Preferred compounds of the formula I are listed below. The hydrochlorides are indicated in each case, but other pharmaceutically acceptable salts are likewise suitable.
1[1-(3,4-dichlorophenyl)-cyclobutyl]-ethylamine.hydrochloride, N-methyl-1-[1-(3,4-dichlorophenyl)-cyclobutyl]ethylamine. hydrochloride,
1-[1-(4-iodophenyl)-cyclobutyl]ethylamine.hydrochloride,
N-methyl-1-(4-iodophenyl)-cyclobutyl]ethylamine.hydrochloride,
N-methyl-1-[1-(2-naphthyl)-cyclobutyl]ethylamine.hydrochloride
1-(1-(4-chlorophenyl)-cyclobutyl]butylamine.hydrochloride,
N-methyl-1-[1-(4-chlorophenyl)-cyclobutyl]butylamine.hydrochloride,
1-[1-(3,4-dichlorophenyl)-cyclobutyl]butylamine.hydrochloride,
N-methyl-1-[1-(3,4-dichlorophenyl)-cyclobutyl]butylamine.hydrochloride,
1-[1-(4-biphenylyl)-cyclobutyl]butylamine.hydrochloride,
1-[1-(4-chloro-3-fluorophenyl)-cyclobutyl]butylamine.hydrochloride,
N-formyl-1-[1(4-chloro-3-fluorophenyl)-cyclobutyl]butylamine,
1-[1-(3-chloro-4-methylphenyl)-cyclobutyl]butylamine.hydrochloride,
N-formyl-1-[1-phenylcyclobutyl]butylamine,
1-[1-(3-trifluoromethylphenyl)-cyclobutyl]butylamine.hydrochloride,
1-[1-(naphth-2-yl)-cyclobutyl]butylamine.hydrochloride,
1-[1-(6-chloronaphth-2-yl)-cyclobutyl]butylamine,
N-methyl-1-[1-(4-chlorophenyl)-cyclobutyl]-2-methylpropylamine.hydrochloride,
1-[1-(4-chlorophenyl)-cyclobutyl]pentylamine.hydrochloride,
N-methyl-1-[1-(4-chlorophenyl)-cyclobutyl]pentylamine.hydrochloride,
N-formyl-1-[1-(4-chlorophenyl)-cyclobutyl]-3-methylbutylamine,
N-methyl-1-[1-(naphth-2-yl)-cyclobutyl]-3-methylbutylamine.hydrochloride,
N-methyl-1-[1-(3,4-dimethylphenyl)-cyclobutyl]-3-methylbutylamine.hydrochloride,
[1-(4-chlorophenyl)-cyclobutyl]-(cyclopropyl)methylamine.hydrochloride,
N-methyl-[1-(4-chlorophenyl)-cyclobutyl]-(cyclopentyl)methylamine.hydrochloride,
[1-(4-chlorophenyl)-cyclobutyl]-(cyclohexyl)methylamine.hydrochloride,
N-methyl-[1-(4-chlorophenyl)-cyclobutyl]-(cyclohexyl)methylamine.hydrochloride,
[1-(3,4-dichlorophenyl)-cyclobutyl]-(cyclohexyl)methylamine.hydrochloride,
N-methyl-[1-(3,4-dichlorophenyl)-cyclobutyl]-(cyclohexyl)methylamine.hydrochloride,
[1-(4-chlorophenyl)-cyclobutyl]-(cyclohexyl)methylamine.hydrochloride,
1-[1-(4-chlorophenyl(-cyclobutyl]-2-cyclopropylethylamine.hydrochloride,
α-[1-(4-chlorophenyl)-cyclobutyl]benzylamine.hydrochloride,
N-methyl-α-[1-(4-chlorophenyl)-cyclobutyl]benzylamine.hydrochloride,
1-[1-(4-chloro-2-fluorophenyl)-cyclobutyl]butylamine,
1-{[1-(3,4-dichlorophenyl)-cyclobutyl]-methyl}propylamine.hydrochloride,
N-ethyl-1-[1-(3,4-dichlorophenyl)-cyclobutyl]ethylamine.hydrochloride.

The preparation of the compounds used according to the invention is illustrated in detail by the examples indicated in DE 32 13 682, which are, however, intended to be merely by way of example.

Thus, the preparation of 1-[1-(3,4-dichlorophenyl)-cyclobutyl]ethylamine is described in Example 1 of DE 32 12 682 as follows:

A solution of 3,4-dichlorobenzyl cyanide (25 g) and 1,3-dibromopropane (15 ml) in dry dimethyl sulfoxide (150 ml) was added dropwise under nitrogen to a stirred mixture of sodium hydride (7.5 g), which was dispersed in mineral oil (7.5 g), and dimethyl sulfoxide (200 ml) at 30–35° C. The mixture was stirred at room temperature for 2 hours, and 2-propanol (8 ml) and then water (110 ml) were added dropwise. The mixture was filtered through diatomaceous earth which is marketed under the proprietary name CELITE, and the solid residue was washed with ether. The ether layer was separated off, washed with water, dried and evaporated. 1-(3,4-dichlorophenyl)-1-cyclobutane-carbonitrile was isolated by distillation (boiling point: 108 to 120° C. under 0.2 mbar. This procedure is a modification of the process described by Butler and Pllatz (J. Org. Chem. 36 No. 9 (1971) 1308).

The 1-(3,4-dichlorophenyl)-1-cyclobutanecarbonitrile (21.7 g) prepared above was dissolved in dry ether (50 ml), and the solution was added under nitrogen to the product of the reaction of gaseous methyl bromide with magnesium turnings (3.9 g) in dry ether (150 ml). The mixture was stirred at room temperature for 2 hours and then refluxed for 2 hours. Crushed ice and then concentrated hydrochloric acid (100 ml) were added, and the mixture was refluxed for 2 hours. The ether layer was separated off, washed with water and aqueous sodium bicarbonate, dried and evaporated. Distillation resulted in 1-acetyl-1-(3,4-dichlorophenyl)cyclobutane (boiling point: 108 to 110° C. under 0.27 mbar).

The 1-acetyl-1-(3,4-dichlorophenyl)cyclobutane (9,1 g) prepared above, formamide (6.5 ml) and 98% formic acid (3 ml) were heated at 180° C. for 16 hours to result in N-formyl-1-[1-(3,4-dichlorophenyl)cyclobutyl]ethylamine. Concentrated hydrochloric acid (20 ml) was added, and the mixture was refluxed for 3 hours. The solution was then cooled and washed with ether, and sodium hydroxide solution was added. The product was extracted with ether, and the ether extract was washed with water, dried and evaporated. 1-[1-(3,4-dichlorophenyl)cyclobutyl]ethylamine was isolated by distillation (boiling point: 112 to 118° C. under 0.27 mbar). The amine was dissolved in 2-propanol and concentrated hydrochloric acid, and the solution was evaporated to dryness to result in 1-[1-(3,4-dichlorophenyl)cyclobutyl]-ethylamine.hydrochloride (melting point: 185 to 195° C.). (Formula III: n=0; $R^1$=methyl; $R^2$, $R^3$ and $R^4$=H; $R^5$=4-Cl; $R^6$=3-Cl).

The compounds indicated hereinafter by way of example are also prepared as described in DE 32 12 682. As the group $R^1$ increases in size, the hydrochlorides of the required compounds become less soluble in the aqueous phase and more soluble in the organic hase so that suitable modifications must be made in the isolation stage, but these are known to a skilled worker.

compressed to tablets containing 50.0 mg of the active ingredient in a tabletting machine.

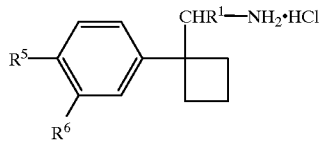

| Ex. | | R$^1$ | R$^5$ | R$^6$ | m.p. (° C.) |
|---|---|---|---|---|---|
| 10 | (a) | Isopropyl | Cl | H | 200–202 |
| 10 | (b) | sec-Butyl | Cl | H | 178–179 |
| 10 | (c) | Isobutyl | Cl | H | 163–165 |
| 10 | (d) | Cyclopentyl | Cl | H | 185–210 |
| 10 | (e) | Phenyl | Cl | H | 271–276 |
| 10 | (f) | 4-Methoxyphenyl | Cl | H | 214–219 |
| 10 | (g) | Cyclohexyl | Cl | H | 206–210 |
| 10 | (h) | Isobutyl | H | H | 210–212 |
| 10 | (i) | Cyclopropyl | Cl | H | 204–206 |
| 10 | (j) | Propyl | Phenyl | H | 235–236 |
| 10 | (k) | Propyl | Methyl | Cl | 214–217 |
| 10 | (l) | Propyl | —(CH=CH$_2$)— | | 157–159 |
| 10 | (m) | Cycloheptyl | Cl | H | 156–162 |
| 10 | (n) | Cyclohexyl | Cl | Cl | 215 |
| 10 | (p) | Methyl | Cl | F | 215–217 |
| 10 | (q) | Propyl | OCH$_3$ | H | 178–179 |
| 10 | (r) | Propyl | Cl | F | 186–188 |
| 10 | (s) | Propyl | Cl | H | 174–175 |
| 10 | (t) | Cyclohexylmethyl | Cl | H | 148–150 |
| 10 | (u) | Cyclopropyl-methyl | Cl | H | 184–185 |
| 10 | (v) | Propyl | —CH=CH—CCl=CH—*) | | |
| 10 | (w) | Propyl | H | CF$_3$ | 126–128 |
| 10 | (x) | 4-Fluorophenyl | Cl | H | 279 |
| 10 | (y)**) | Methyl | —C=C—CH=CH— (benzo-fused) | | 248–262 |

*) Boiling point of the free base 168° C./0.06 mbar
**) Diethylene glycol dimethyl ether replaced by ethylene glycol dimethyl ether The preparation of further compounds is likewise described in DE 32 12 682.

The preparation of salts of the compounds according to the invention is likewise illustrated in DE 32 12 682, where equimolar amounts of the base and of the acid were taken up in a solvent. The salt was then obtained from the solvent in a conventional way.

Pharmaceutical preparations which contain any of the compounds of the formula I mentioned above are prepared as described in DE 32 12 682.

Tablets are produced from the following ingredients:

| | Parts by weight |
|---|---|
| Active ingredient | 50.0 |
| Lactose | 78.5 |
| Polyvinylpyrrolidone | 5.0 |
| Corn starch | 15.0 |
| Magnesium stearate | 1.5 |

The active ingredient, the lactose and part of the starch are mixed and granulated with a solution of the polyvinylpyrrolidone in ethanol. The granules are mixed with the stearic acid and the remainder of the starch, and the mixture is Capsules are produced in the following way: a mixture of the active ingredient (45 parts by weight) and lactose powder (205 parts by weight) is packed in hard gelatin capsules so that each capsule contains 45 mg of the active ingredient.

Tablets provided with a coating which dissolves only in the intestine are produced by coating the tablets with a thin layer of shellac lacquer, followed by 20 coatings of cellulose acetate phthalate, in a manner know to the skilled worker. The capsules can be provided with a coating which dissolves only in the intestine in a similar way.

Ampoules which contain a solution of water-soluble compounds of the present invention suitable for injection are produced from the following ingredients:

| | |
|---|---|
| Active ingredient | 1100 g |
| Mannitol | 1100 g |
| Water, freshly distilled, | ad 1 liter |

The active ingredient and mannitol are dissolved in part of the water, and the volume of the solution is adjusted to 1 liter. The resulting solution is sterilized by filtration and dispensed into sterile ampoules, each of which contains 1.65 ml of the solution.

Suppositories are produced by incorporating 100 parts by weight of the finely ground active ingredient in 1214 parts by weight of triglyceride suppository base, and the mixture is shaped to suppositories, each of which contains 100 mg of the active ingredient.

The compounds of the formula I are suitable for treating obesity and its accompanying disorders. Disorders accompanying obesity which should be mentioned in particular are: diabetes, hypertension and hypercholesterolemia.

The effect of these compounds can be demonstrated by in vivo animal experiments. These revealed that, surprisingly, compounds of the formula III with n=O, $R^1$=isobutyl, $R^2$=H, $R^4$=H, $CH_3$, $R^5$=Cl, $R^6$=H lead to a large increase in the extracellular levels of the endogenous neurotransmitters serotonin and norepinephrine in the CNS. Compounds where $R^4$ is a hydrogen atom in particular show a good effect in these experiments.

The utility of the compounds of the formula III for treating obesity is illustrated by the following test which measures the extracellular 5-hydroxytryptamine levels (5 HT levels) in the rat hypothalamus after direct infusion of the compounds of the formula III where:

A) $R^1$ is isobutyl, $R^2$ is H, $R^3$ is methyl, $R^4$ is H, $R^5$ is 4-chloro, $R^6$ is H and X is H, and B) $R^1$ is isobutyl, $R^2$ is H, $R^3$ is H, $R^4$ is H, $R^5$ is 4-chloro, $R^6$ is H and X is H.

The compound N,N-dimethyl-1-[1-(4-chlorophenyl)cyclobutyl]-3-methylbutylamine hydrochloride, which is referred to as C and was disclosed in WO90/06110, was tested likewise.

Male Sprague-Dawley albino rats (Harlan Labs, Indianapolis, Ind.), which weighed 250–350 g were housed singly with a reversed day/night cycle (darkness from 9:30 to 21:30). Water and feed were freely available. The animals were anesthetized with a combination of ketamine and xylazine and fastened in a head stereotaxy frame with the skull in a level position. Guide needles for dialysis tubes (stainless steel tubes, size 22) were implanted through the diencephalon. The co-ordinates, taken from Paxinos and Watson, The Rat Brain in Stereotaxic Co-ordinates, 2nd Edition, 1986, were: AP+6.2, ML+1.0, relative to the interaural line (IAL), and DV 3.0 under the surface of the skull. The needles were fastened with 4 skull screws and dental cement. Before starting an experiment, the animals were allowed to recover from the operation for at least one week.

Concentric dialysis tubes were constructed using stainless steel tubes and hollow silica fibers. The total length of the tube was adjusted so that the tip was located in the hypothalamus (target for the tube tip: DV 9.7 under the skull). The exchange surface of the tubes was a hollow nitrocellulose fiber 2.5 mm long (0.2 mm external diameter, molecular weight cut-off 6000; Spectrum Medical Industries, Los Angeles, Calif.). The average recovery of the tubes was 18.7+1.7% (n=4) at a flow rate of 1 $\mu$l/min.

One day before an experiment, the rats were briefly sedated with the volatile anesthetic methoxyflurane, and a tube was slowly lowered into the diencephalon. The tube was cemented into the guide needle and additionally protected by a cylindrical plastic sleeve. The animals were placed in a test chamber and fastened to a liquid tilting device so that they were freely movable. The tubes were continuously perfused with artificial CSF (aCSF; 147 mM NaCl, 4.0 mM KCl, 1.8 mM $CaCl_2$, unadjusted pH 6.3) at a rate of 1.0 $\mu$l/min by means of a microinjection pump (CMA/100), Carnegie-Medicin, Stockholm, Sweden). Samples were collected during the dark period from the next morning onwards.

Experimental manipulations were carried out after stable 5-HT levels were obtained (less than+10% variation for 4 consecutive samples).

The samples were analyzed by HPLC with electrochemical detection.

BRIEF DESCRIPTION OF THE DRAWING

FIG. A graphically shows the effectiveness of compound A.

FIG. B graphically shows the effectiveness of compound B.

FIG. C graphically shows the effectiveness of compound C.

Compounds A, B or C were administered into the hypothalamus by reverse dialysis infusion over a period of 2 hours, while samples for extracellular 5-HT were taken using the same dialysis tube.

A (10 $\mu$M) caused a persistent 5-fold increase in 5-HT in the hy<pothalamus (F(1.9)=17.9, p<0.0022), see FIG. A.

B (10 $\mu$M) produced a persistent two- to three-fold increase in 5-HT in the hypothalamus (F(1.15)=21.1, p<0.0004), see FIG. B.

During infusion of C in a concentration of 2 mM in aCSF there was a persistent four- to five-fold increase in the extracellular 5-HT (F(1.7)=43.2, p<0.0003), see FIG. C.

C was far less effective than compounds A and B according to the invention. Infusion of A (10 $\mu$M) and B (10 $\mu$M) produced increases of 350% and 150%, respectively, above the base line, while millimolar concentrations of C (2 mM) were required to produce a comparable effect on the extracellular 5-HT levels.

An enhancement of the 5-hydroxytryptaminergic effect assists the inhibitory effect of various drugs on food intake (Hypothalamic Serotonin: Pharmacological, Biochemical and Behavioural Analyses of its Feeding—Suppressive Action: Clin. Neuropharmacol. 11 (1), pages 551–571, Leibovitz et al.). These data therefore show that the activity of A and B is 200 times that of C. These compounds are accordingly superior in respect of their efficacy for treating obesity.

We claim:

1. A method for treating obesity and disorders associated with obesity, which comprises administering an effective amount of a cyclobutylalkylamine of the formula IIIa

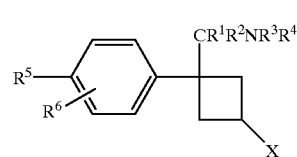

IIIa wherein $R^1$ is $C_1$–$C_4$-alkyl, $R^2$, $R^3$, $R^6$ are hydrogen, $R^4$ is hydrogen or methyl, $R^5$ is Cl or Br, and X is hydrogen or hydroxyl, or a pharmaceutically suitable salt thereof, to a host.

2. The method of claim 1, wherein $R^1$ is isobutyl, $R^2$ and $R^3$ are hydrogen, $R^4$ is hydrogen or methyl, $R^5$ is chloro, and $R^6$ and X are hydrogen.

3. The method of claim 1, wherein the cyclobutylalkylamine of the formula IIIa is (R)-(+)-N-{1-[1-(4- chlorophenyl)cyclobutyl]-3-methylbutyl}-N-methylamine, (S)-(−)-N-{1−[1-(4-chlorophenyl)cyclobutyl ]-3-methylbutyl}-N-methylamine, (R)-(+)-1-[1-(4-chlorophenyl) cyclobutyl]-3-methylbutylamine or (S)-(−)-1-[1-(4-chlorophenyl) cyclobutyl)cyclobutyl]-3-methylbutylamine.

4. A method for treating obesity and disorders associated with obesity, which comprises administering an effective amount of N-methyl-1-[1-(4-chlorophenyl)cyclobutyl]-3-methylbutylamine or a pharmaceutically suitable salt thereof to a host.

5. A method for treating obesity and disorders associated with obesity, which comprises administering an effective amount of a cyclobutylalkylamine of the formula I

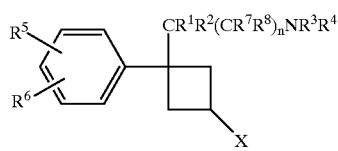

where
n is 0 or 1,
$R^1$ is, when n is 0, a straight-chain or branched-chain alkyl group having 1 to 6 carbon atoms, a cycloalkyl group having 3 to 7 carbon atoms, a cycloalkylalkyl group in which the cycloalkyl group contains 3 to 6 carbon atoms and the alkyl group contains 1 to 3 carbon atoms, an alkenyl or an alkynyl group having 2 to 6 carbon atoms, it being possible for the alkyl group, the cycloalkyl group, the cycloalkylalkyl group, the alkenyl group or the alkynyl group to carry at least one substituent which is selected from the group consisting of hydroxyl and acyloxy, alkoxy groups, unsubstituted or substituted by hydroxyl, oxo, alkoxy, carbamoyl, carbocyclic groups, cycloalkoxy groups having 3 to 6 carbon atoms, alkylenedioxy groups, oxo- and groups of the formula $S(O)_pR^5$, where p is 0, 1 or 2, and $R^5$ is an alkyl group having 1 to 3 carbon atoms, it being possible for the aliphatic group to be substituted by other substituents selected from carbocyclic groups having 3 to 6 carbon atoms and halogen atoms, or a group of the formula

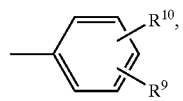

where $R^9$ and $R^{10}$, which can be identical or different, are a hydrogen atom, a halogen atom or an alkoxy group having 1 to 3 carbon atoms, and, when n is 1, a hydrogen atom or an alkyl group having 1 to 3 carbon atoms,
$R^2$ is a hydrogen atom or an alkyl group having 1 to 3 carbon atoms,
$R^3$ is a hydrogen atom,
$R^4$ is a hydrogen atom, a straight-chain or branched-chain alkyl group having 1 to 4 carbon atoms, an alkenyl group having 3 to 6 carbon atoms, an alkynyl group having 3 to 6 carbon atoms, or a cycloalkyl group having 3 to 7 carbon atoms, or
$R^4$ is CHO,
$R^5$ and $R^6$, which can be identical or different, are a hydrogen atom, a halogen atom, a trifluoromethyl group, an alkyl group having 1 to 3 carbon atoms, an alkoxy or alkylthio group having 1 to 3 carbon atoms or a phenyl group, or together with the carbon atoms to which they are bonded form a second benzene ring which is unsubstituted or substituted by one or more halogen atoms, one alkyl or alkoxy group having 1 to 4 carbon atoms, or the substituents in the second benzene ring form, together with the two carbon atoms to which they are bonded, another benzene ring, and
$R^7$ and $R^8$, which can be identical or different, are a hydrogen atom or an alkyl group having 1 to 3 carbon atoms, and
X is a hydrogen atom or a hydroxyl group, or a pharmaceutically suitable salt thereof, to a host.

6. The method of claim 5, wherein X is a hydrogen atom.

7. The method of claim 6, wherein $R^1$ is methyl, ethyl, propyl, isopropyl, butyl, isobutyl, sec-butyl, cyclopropyl, cyclobutyl, cyclopentyl, cyclohexyl, cycloheptyl, cyclopropylmethyl, cyclobutylmethyl, cyclopentylmethyl, cyclohexylmethyl or phenyl.

8. The method of claim 5, wherein n is 0, $R^1$ is a straight-chain or branched-chain alkyl group having 1 to 4 carbon atoms, a cycloalkyl group having 3 to 7 carbon atoms, a cycloalkylmethyl group in which the cycloalkyl ring contains 3 to 6 carbon atoms, or a group of the formula

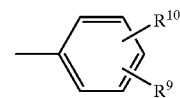

in which $R^9$ and/or $R^{10}$ are a hydrogen atom, a fluorine atom or a methoxy group, and $R^2$ is a hydrogen atom or a methyl group.

9. The method of claim 5, wherein n is 1, $R^1$ is a hydrogen atom or methyl and $R^2$ is a hydrogen atom.

10. The method of claim 5, wherein $R^4$ is a hydrogen atom, methyl, ethyl or formyl.

11. The method of claim 5, wherein $R^5$ is chlorine and $R^6$ is hydrogen or chlorine.

12. The method of claim 5, wherein n is 0.

13. A method for treating obesity, which comprises administering an effective amount of a cyclobutylalkylamine of the formula IIIa

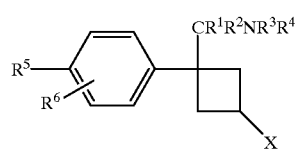

wherein $R^1$ is $C_1$–$C_4$-alkyl, $R^2$, $R^3$, $R^6$ are hydrogen, $R^4$ is hydrogen or methyl, $R^5$ is Cl or Br, and X is hydrogen or hydroxyl, or a pharmaceutically suitable salt thereof, to a host.

14. The method of claim 13, wherein
$R^1$ is isobutyl,
$R^2$ and $R^3$ are hydrogen,
$R^4$ is hydrogen or methyl,
$R^5$ is chloro, and
$R^6$ and X are hydrogen.

15. The method of claim 13, wherein the compound of the formula IIIa is 1-[1-(4-chlorophenyl)cyclobutyl]-3-methylbutylamine.

16. The method of claim 13, wherein the compound of the formula IIIa is N-methyl-1-[1-(4-chlorophenyl)cyclobutyl]-3-methylbutylamine.

17. A method for treating obesity, which comprises administering an effective amount of a cyclobutylalkylamine of the formula I

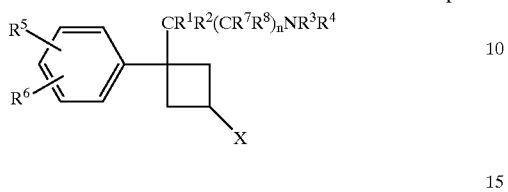

where n is 0 or 1, $R^1$ is, when n is 0, a straight-chain or branched-chain alkyl group having 1 to 6 carbon atoms, a cycloalkyl group having 3 to 7 carbon atoms, a cycloalkylalkyl group in which the cycloalkyl group contains 3 to 6 carbon atoms and the alkyl group contains 1 to 3 carbon atoms, an alkenyl or an alkynyl group having 2 to 6 carbon atoms, it being possible for the alkyl group, the cycloalkyl group, the cycloalkylalkyl group, the alkenyl group or the alkynyl group to carry at least one substituent which is selected from the group consisting of hydroxyl and acyloxy, alkoxy groups, unsubstituted or substituted by hydroxyl, oxo, alkoxy, carbamoyl, carbocyclic groups, cycloalkoxy groups having 3 to 6 carbon atoms, alkylenedioxy groups, oxo- and groups of the formula $S(O)_pR^5$, where p is 0, 1 or 2, and $R^5$ is an alkyl group having 1 to 3 carbon atoms, it being possible for the aliphatic group to be substituted by other substituents selected from carbocyclic groups having 3 to 6 carbon atoms and halogen atoms, or a group of the formula

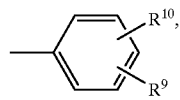

where $R^9$ and $R^{10}$, which can be identical or different, are a hydrogen atom, a halogen atom or an alkoxy group having 1 to 3 carbon atoms, and, when n is 1, a hydrogen atom or an alkyl group having 1 to 3 carbon atoms, $R^2$ is a hydrogen atom or an alkyl group having 1 to 3 carbon atoms, $R^3$ is a hydrogen atom, $R^4$ is a hydrogen atom, a straight-chain or branched-chain alkyl group having 1 to 4 carbon atoms, an alkenyl group having 3 to 6 carbon atoms, an alkynyl group having 3 to 6 carbon atoms, or a cycloalkyl group having 3 to 7 carbon atoms, or $R^4$ is CHO, $R^5$ and $R^6$, which can be identical or different, are a hydrogen atom, a halogen atom, a trifluoromethyl group, an alkyl group having 1 to 3 carbon atoms, an alkoxy or alkylthio group having 1 to 3 carbon atoms or a phenyl group, or together with the carbon atoms to which they are bonded form a second benzene ring which is unsubstituted or substituted by one or more halogen atoms, one alkyl or alkoxy group having 1 to 4 carbon atoms, or the substituents in the second benzene ring form, together with the two carbon atoms to which they are bonded, another benzene ring, and $R^7$ and $R^8$ which can be identical or different, are a hydrogen atom or an alkyl group having 1 to 3 carbon atoms, and X is a hydrogen atom or a hydroxyl group, or a pharmaceutically suitable salt thereof, to a host.

18. The method of claim 14, the cyclobutylalkylamine of the formula IIIa is (R)-(+)-N-{1-[1-(4-chlorophenyl)cyclobutyl[-3-methylbutyl}-N-methylamine, (S)-(−)-N-{1-[1- (4-chlorophenyl)cyclobutyl ]3- methylbutyl}-N-methylamine, (R)-(+)-1-[1-(4-chlorophenyl) cylcobutyl]-3-methylbutylamine or (S)-(+)-1-[1-(4-chlorophenyl) cyclobutyl[-3-methylbutylamine.

19. The method of claim 18, wherein $R^1$ is methyl, ethyl, propyl, isopropyl, butyl, isobutyl, sec-butyl, cyclopropyl, cyclobutyl, cyclopentyl, cyclohexyl, cycloheptyl, cyclopropylmethyl, cyclobutylmethyl, cyclopentylmethyl, cyclohexylmethyl or phenyl.

20. The method of claim 17, wherein n is 0, $R^1$ is a straight-chain or branched-chain alkyl group having 1 to 4 carbon atoms, a cycloalkyl group having 3 to 7 carbon atoms, a cycloalkylmethyl group in which the cycloalkyl ring contains 3 to 6 carbon atoms, or a group of the formula

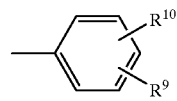

in which $R^9$ and/or $R^{10}$ are a hydrogen atom, a fluorine atom or a methoxy group, and $R^2$ is a hydrogen atom or a methyl group.

21. The method of claim 17, wherein n is 1, $R^1$ is a hydrogen atom or methyl and $R^2$ is a hydrogen atom.

22. The method of claim 17, wherein $R^4$ is a hydrogen atom, methyl, ethyl or formyl.

23. The method of claim 17, wherein $R^5$ is chlorine and $R^6$ is hydrogen or chlorine.

24. The method of claim 17, wherein n is 0.

* * * * *

UNITED STATES PATENT AND TRADEMARK OFFICE
CERTIFICATE OF CORRECTION

PATENT NO. : 6,127,424
DATED : October 3, 2000
INVENTOR(S) : Martin et al.

It is certified that error appears in the above-identified patent and that said Letters Patent is hereby corrected as shown below:

Column 13, claim 3,
Line 2, "cyclobutyl ]" should be -- cyclobutyl] --.
Line 5, "cyclobutyl)cyclobutyl]" should be -- cyclobutyl] --.

Column 16, claim 18,
Line 24, " cyclobutyl  ]3– methylbutyl}" should be -- cyclobutyl]3-methylbutyl} --.

Column 16, claim 19,
Line 28, "claim 18" should be -- claim 26 --.

Add claims 25 and 26 as follows:

-- 25. A method for treating obesity and disorders associated with obesity, which comprises administering an efecitve amount of 1-[1-4(chlorophenyl)cyclobutyl]-3–methylbutylamine or a pharmaceutically suitable salt thereof to a host.

26. The method of claim 17, wherein X is a hydrogen atom. --

Signed and Sealed this

Twenty-fifth Day of September, 2001

Attest:

NICHOLAS P. GODICI
Attesting Officer    Acting Director of the United States Patent and Trademark Office